(12) United States Patent
Liu et al.

(10) Patent No.: US 10,436,696 B2
(45) Date of Patent: Oct. 8, 2019

(54) METHODS AND SYSTEMS FOR DETERMINING GAS PERMEABILITY OF A SUBSURFACE FORMATION

(71) Applicant: Saudi Arabian Oil Company, Dharan (SA)

(72) Inventors: Hui-Hai Liu, Houston, TX (US); Bitao Lai, Houston, TX (US); Jilin Jay Zhang, Houston, TX (US); Daniel Georgi, Houston, TX (US); Xinwo Huang, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/056,596

(22) Filed: Aug. 7, 2018

(65) Prior Publication Data

US 2018/0340878 A1 Nov. 29, 2018

Related U.S. Application Data

(62) Division of application No. 15/378,305, filed on Dec. 14, 2016.

(Continued)

(51) Int. Cl.
*G01N 15/08* (2006.01)
*G01N 33/24* (2006.01)

(52) U.S. Cl.
CPC ......... *G01N 15/0826* (2013.01); *G01N 33/24* (2013.01)

(58) Field of Classification Search
CPC ........... G01N 15/0826; G01N 15/0806; G01N 15/08; G01N 33/24; G01N 33/241
See application file for complete search history.

(56) References Cited

U.S. PATENT DOCUMENTS

| | | |
|---|---|---|
| 4,253,327 A | 3/1981 | Wiley |
| 4,996,872 A | 3/1991 | Mueller et al. |

(Continued)

FOREIGN PATENT DOCUMENTS

| | | |
|---|---|---|
| CN | 204177799 U | 2/2015 |
| WO | WO2014123966 A1 | 8/2014 |

OTHER PUBLICATIONS

Alnoaimi et al., Characterization and Measurement of Multi-Scale Gas Transport in Shale Core Samples, Aug. 25-27, 2014, URTeC: 1920820, Unconventional Resources Technology Conference, Denver, Colorado, 19 pp. (Year: 2014).*

(Continued)

*Primary Examiner* — Toan M Le
(74) *Attorney, Agent, or Firm* — Bracewell LLP; Constance G. Rhegergen; Vivek P. Shankam

(57) ABSTRACT

Methods and systems for determining permeability, as a function of pore pressure, and porosity of a subsurface formation. The method includes positioning a sample in a sample assembly comprising of a gas and a pressure gauge, inside a pressure vessel comprising gas or liquid and a pressure gauge, measuring a first gas pressure, $p_i$, of the sample inside the pressure vessel, applying a second gas pressure, $p_o$, to the pressure vessel, the second gas pressure being greater than the first gas pressure, measuring a third gas pressure, p, at time, t, at location, x, from the inlet of sample inside the pressure vessel, determining a total gas mass per unit volume of the subsurface formation, m, and determining the permeability, k, of the subsurface formation as a function of pore pressure based at least in part on the first gas pressure, the second pressure, the third gas pressure, and the gas density, with a single test run.

13 Claims, 8 Drawing Sheets

Related U.S. Application Data

(60) Provisional application No. 62/267,091, filed on Dec. 14, 2015.

(56) References Cited

U.S. PATENT DOCUMENTS

| | | | |
|---|---|---|---|
| 5,297,420 A * | 3/1994 | Gilliland | G01N 15/08 73/38 |
| 5,731,511 A | 3/1998 | Roque et al. | |
| 6,591,661 B2 | 7/2003 | Davey | |
| 7,131,317 B2 | 11/2006 | Roland et al. | |
| 2015/0354352 A1 | 12/2015 | Moustafa et al. | |
| 2017/0167964 A1 | 6/2017 | Liu et al. | |

OTHER PUBLICATIONS

Clarkson, C.R. et al.; "Use of Pressure- and Rate-Transient Techniquest for Analyzing Core Permeability Tests for Unconventional Reservoirs" SPE 154815, Americas Unconventional Resources Conference Jun. 5-7, 2012; pp. 1-22.

Heller, Rob et al.; "Experimental investigation of matrix permeability of gas shales" AAPG Bulletin, V. 98, No. 5 (May 2014); pp. 975-995.

Liu, Hui-Hai et al.; "An Innovative Laboratory Method to Measure Pore-Pressure-Dependent Gas Permeability of Shale: Theorty and Numerical Experiments" SPE 191123, SPE Reservoir Evaluation & Engineering, 2018; pp. 1-10.

Alnoaimi, K. R. et al.:"Experimental and numerical analysis of gas transport in shale including the role of sorption." SPE Annual Technical Conference and Exhibition. Society of Petroleum Engineers, 2013; pp. 1-16.

Civan, F. et al.: "Comparison of Shale Permeability to Gas Determined by Pressure-Pulse Transmission Testing of Core Plugs and Crushed Samples" SPE-178571-MS/URTeC:2154049, Unconventional Resources Technology Conference TX, USA Jul. 20-22, 2015 (13 pgs).

Civan, F. et al.: "Determining shale permeability to gas by simultaneous analysis of various pressure tests." SPE 144253; SPE Unconventional Gas Conference, Journal 17.03 (2012); pp. 717-726.

Darabi, et al.: "Gas flow in ultra-tight shale strata." Journal of Fluid Mechanics 710.1 (2012): pp. 641-658.

International Search Report and Written Opinion for PCT/US2016/066591; International Filing Date Dec. 14, 2016; Report dated Feb. 16, 2017 (pp. 1-14).

Jones, S. C. "A technique for faster pulse-decay permeability measurements in tight rocks." SPE 28450; SPE Annual Technical Conference & Exhibition (1994); pp. 19-26.

* cited by examiner

METHODS AND SYSTEMS FOR DETERMINING GAS PERMEABILITY OF A SUBSURFACE FORMATION

CROSS-REFERENCE TO RELATED PATENT APPLICATIONS

This application claims priority from U.S. patent application Ser. No. 15/378,305, filed Dec. 14, 2016, which claims priority from Provisional Application No. 62/267,091, filed Dec. 14, 2015, both titled "METHODS AND SYSTEMS FOR DETERMINING PORE PRESSURE-DEPENDENT GAS PERMEABILITY OF A SUBSURFACE FORMATION," the entire contents of which is incorporated herein by reference.

TECHNICAL FIELD

Example embodiments relate to methods and systems for determining permeability and porosity of a subsurface rock formation using pore gas pressure.

BACKGROUND

Unlike conventional reservoirs, pores in shale formations are extremely small, typically on the order of nanometers. In these nano pores, a non-negligible portion of gas molecules collides more often with the pore wall than with other molecules, and thus so-called "slip flow" and Knudsen diffusion occur. Previous studies on gas flow in shale matrix found that the gas permeability in shale is a function of the pore gas pressure because the slip flow and Knudsen diffusion effect becomes significant when the pore gas pressure is relatively low.

Shale gas permeability as a function of pore gas pressure, resulting from "slip flow" and diffusion processes, is critical for characterizing and modeling gas flow in a shale gas reservoir. However, this important pore gas pressure-dependency is hardly considered in practice because of the lack of a practical and efficient technique that can be used routinely for determining the pressure-dependent shale gas permeability.

Pressure dependence has a significant impact on predicted gas-production rate. There are currently two approaches to measure the pressure dependence of gas permeability in the laboratory. The first one is to simply perform a number of pulse-decay permeability tests under different gas pressures. Then, these tests will provide gas permeability values for a number of gas pressures. Initially, the system is in equilibrium with a given gas pressure. A small pressure pulse is then introduced into the upstream gas reservoir, such that the pulse does not have a significant disturbance to the gas pressure in the system. The pressures at the two gas reservoirs are monitored as a function of time. The pressure evolution results are fitted using analytical solutions, with permeability being a fitting parameter. However, it generally takes a relatively long time to equilibrate the test system from one test pressure to the next one.

The other approach to determine the pressure dependence is to first develop a formulation of gas permeability as a function of gas pressure and then estimate values for parameters in the formulation by numerically matching the relevant test results under different gas pressure conditions. Test results are generally different from pulse-decay tests in which the pressure pulse is not limited to a small one because numerical model is flexible enough to incorporate the pulse disturbance to the system. However, non-uniqueness of parameter estimation is always a problem for inverse modeling. Also the accuracy of estimated results from this approach is ultimately determined by that of the used formulation of gas permeability as a function of gas pressure that is not fully established yet.

SUMMARY

Example embodiments disclosed provide a new method to measure relationship between shale gas permeability and pore gas pressure. The development is based on a new analytical solution to one-dimensional gas flow under certain boundary and initial conditions. The advantages of the disclosed approach over the currently available ones include that it directly measures the relationship using a single test run and without any presumption regarding the form of parametric relationship between gas permeability and pressure. In addition, the current approach allows for estimating both shale permeability and porosity at the same time from the related measurements.

One example embodiment is a transient flow method for determining permeability of a subsurface formation. The method includes extracting a sample of the subsurface formation, positioning the sample in a pressure vessel comprising a type of natural or man-made gas or liquid and a pressure gauge, measuring a first pore gas pressure, $p_i$, or the initial pore gas pressure of the sample inside the pressure vessel, applying a second pore gas pressure, $p_o$, to the inlet of the sample within pressure vessel, the second pore gas pressure being greater than the first pore gas pressure ($p_o > p_i$), measuring a third pore gas pressure, p, at location x as a function of time t along the sample in the pressure vessel, determining a total gas mass per unit volume of the subsurface formation, m, and, determining the permeability function, k(p), (hereinafter referred to as permeability, and k) of the subsurface formation from gas transport parameter D(p), based at least in part on the first pore gas pressure, the second pressure, the third pore gas pressure as a function of time, and the gas density, with a single test run. The relationship between D(p) and permeability is given in Equation 9 below. The method may also include determining the gas transport parameter of the subsurface formation, D(p), using a first formula:

$$D(p) = -\frac{\int_{p_i}^{p} \frac{\lambda}{2} \frac{dm}{dp} dp}{\frac{dp}{d\lambda}}$$

where $p_i$ is the first pore gas pressure inside the sample before the second pore gas pressure $p_o$ is applied, p is the third pore gas pressure at location x at time t, m is the gas density or total gas mass per unit volume of the subsurface formation, and $\lambda$ is an independent variable calculated using the formula $xt^{-1/2}$. Then permeability may be determined from D(p) using Equation 9.

The method may also include determining the total gas mass per unit volume of the subsurface formation, m, using a second formula:

$$m = \phi\rho + (1-\phi)\rho_a$$

where $\phi$ is porosity of the subsurface formation, $\rho$ is gas density of the free gas, and $\rho_a$ is adsorbed gas mass per unit volume of the subsurface formation.

The method may also include determining the porosity $\phi$ of the subsurface formation using a third formula:

$$\phi = \frac{B - A\int_{p_i}^{p_0} \lambda \frac{d\rho_a}{dp} dp}{A\int_{p_i}^{p_0} \lambda \frac{d(\rho - \rho_a)}{dp} dp}$$

where A is a cross-sectional area of the sample, and B is a slope of a curve of the cumulative gas flow into the sample at x=0 (sample inlet) versus $t^{1/2}$.

The method may also include determining the slope of the curve, B, using a fourth formula:

$$B = A\int_{p_i}^{p_0} \lambda \frac{dm}{dp} dp$$

Another example embodiment is a non-transitory computer-readable medium having computer executable instructions that cause a computer to perform the operations of reading a measurement of a first pore gas pressure, $p_i$, of a sample inside a pressure vessel comprising a sample assembly of a subsurface formation, a type of natural or man-made gas or liquid, and a pressure gauge, reading a measurement of a second pore gas pressure, $p_o$, applied to the inlet of the sample, the second pore gas pressure being greater than the first pore gas pressure, reading a measurement of a third pore gas pressure, p, as a function of time t, at location x from the end of the sample close to the inlet in the pressure vessel (hereinafter referred to "location x"), determining a total gas mass per unit volume of the subsurface formation, m, and determining a permeability of the subsurface formation, k, based at least in part on the first pore gas pressure, the third pore gas pressure, and the gas density, with a single test run.

The computer executable instructions further cause the computer to perform the operation of determining the transport parameter of the subsurface formation D(p) using a first formula:

$$D(p) = -\frac{\int_{p_i}^{p} \frac{\lambda}{2} \frac{dm}{dp} dp}{\frac{dp}{d\lambda}}$$

where $p_i$ is the first pore gas pressure inside the pressure vessel before the second pore gas pressure $p_o$ is applied, p is the third pore gas pressure at location x at time t, m is the total gas mass per unit volume of the subsurface formation, and $\lambda$ is an independent variable calculated using the formula $xt^{-1/2}$. Then permeability may be determined from D(p) using Equation 9.

The computer executable instructions further cause the computer to perform the operation of determining the total gas mass per unit volume of the subsurface formation, m, using a second formula:

$$m = \phi\rho + (1-\phi)\rho_a$$

where $\phi$ is porosity of the subsurface formation, $\rho$ is gas density of the free gas, and $\rho_a$ is adsorbed gas mass per unit volume of the subsurface formation.

The computer executable instructions further cause the computer to perform the operation of determining the porosity $\phi$ of the subsurface formation using a third formula:

$$\phi = \frac{B - A\int_{p_i}^{p_0} \lambda \frac{d\rho_a}{dp} dp}{A\int_{p_i}^{p_0} \lambda \frac{d(\rho - \rho_a)}{dp} dp}$$

where A is a cross-sectional area of the sample, and B is a slope of a curve of the cumulative gas flow into the sample at x=0 (the sample inlet) versus $t^{1/2}$.

The computer executable instructions further cause the computer to perform the operation of determining the slope of the curve, B, using a fourth formula:

$$B = A\int_{p_i}^{p_0} \lambda \frac{dm}{dp} dp$$

Another example embodiment is an apparatus for determining the permeability of a subsurface formation. The apparatus includes a first sleeve having a length, a diameter, a first open end, and a second open end, a first end piece adapted to be inserted into the first open end and a second end piece adapted to be inserted into the second open end of the first sleeve, a first hole formed through the first sleeve and into a body of the sample, a half sleeve disposed on the first sleeve, the half sleeve having an assembly on a second hole corresponding to the first hole on the first sleeve, consisting of a tubing that connects to a pressure gauge, the tubing passing the second hole, inserted through the first hole, and into the body of the sample, an anchoring device for securing the tubing to the first sleeve and half sleeve, thereby forming an assembly, and a pressure vessel for receiving the assembly, the pressure vessel comprising a fluid and a plurality of pressure taps, wherein at least one of the pressure taps is coupled to the pressure gauge in the aforementioned tubing.

According to one example embodiment, the first sleeve and the half sleeve comprise at least one of rubber and a polymeric material. According to one example embodiment, an inner diameter of the half sleeve is slightly smaller than the outer diameter of the first sleeve. According to one example embodiment, a length of the half sleeve is equal to or less than the length of the first sleeve. According to one example embodiment, the fluid comprises natural gas, water, or oil. According to one example embodiment, the tubing may also include a temperature gauge. According to one example embodiment, pressure gauge may be coupled to the pressure tap using a flexible line. According to one example embodiment, the apparatus may further include an inlet pump configured to pump gas from a first gas tank into the pressure vessel, and an outlet pump configured to store gas from the pressure vessel into a second gas tank.

DETAILED DESCRIPTION

Figure 1:
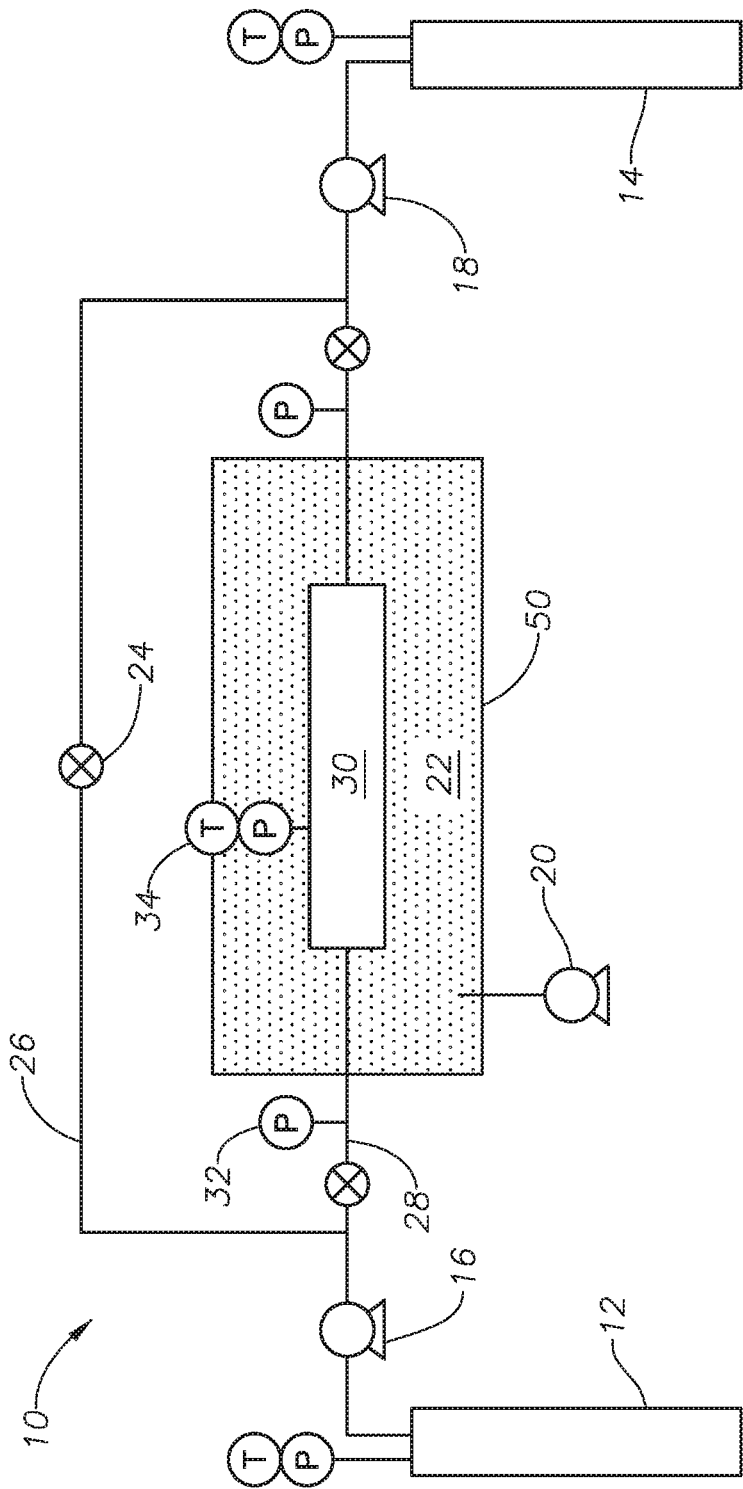
FIG. 1 illustrates an example system for determining permeability and porosity of a subsurface formation, according to one example embodiment of the disclosure.
Figure 2A:
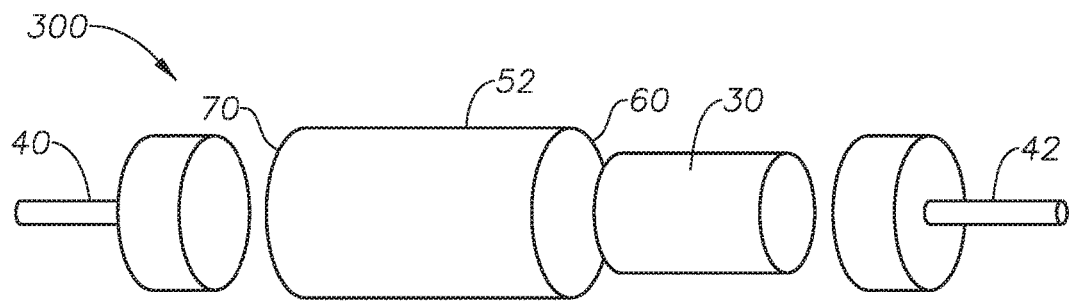
FIGS. 2A-2D illustrate an example apparatus for determining permeability and porosity of a subsurface formation, according to one example embodiment of the disclosure.
Figure 2B:
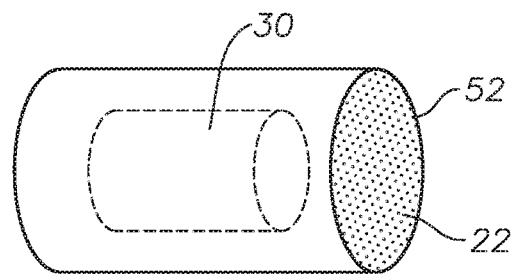
Figure 2C:
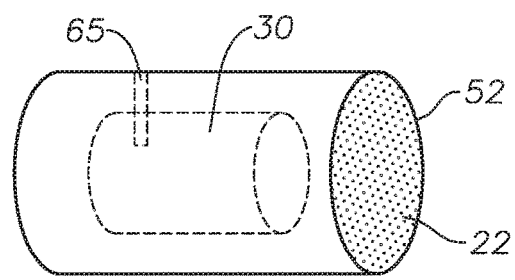
Figure 2D:
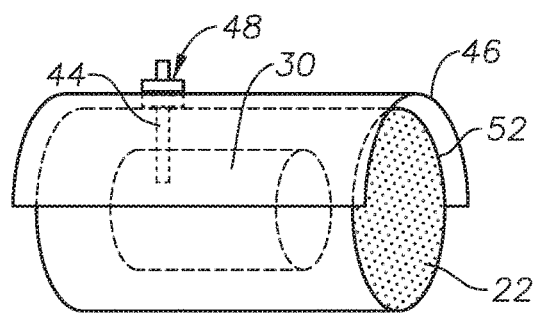

Turning now to the figures, FIG. 1 illustrates an example system 10 for determining permeability function, k(p), (hereinafter referred to as permeability, and k) and porosity of a subsurface formation, according to some example embodiments of the disclosure. System 10 includes a subsurface formation sample assembly 300 (as shown in FIG. 2), inside which is a sample 30, such as a shale sample or a limestone sample or a sandstone sample, in the form of a cylinder or column (referred to as column hereinafter), that may be extracted from the subsurface for determining characteristics of the formation. Sample assembly 300 is introduced in a pressure vessel 50 that may contain a confining fluid 22, such as gas or a water-based fluid or an oil-based fluid. However, example embodiments described herein refer to systems with oil as the confining fluid. The centerpiece of the measurement system is the sample assembly 300 connected to the pumps through the pressure lines with all monitoring and regulating devices; and the pressure vessel 50 provides the confining pressure to the sample assembly 300 and the interfaces to the tubing and lines of measurements via various types of couplings.

System 10 includes an inlet pump 16 configured to pump gas from a first gas tank 12 into the core sample assembly 300, and an outlet pump 18 configured to pump gas from a second gas tank 14 into core sample assembly 300. Both pumps may include precise pressure and flowrate control and measurement. Pressure vessel 50 may be equipped with a hydraulic pump 20 that may pump oil 22 into and may include apparatus that monitor and regulate the pressure within the pressure vessel 50. High accuracy temperature and pressure gauge 34 is connected to rock sample and 32 to the inlet of core sample assembly 300; both of them having high accuracy transducers to measure temperature and pressure, respectively in real-time. An inlet 28 to the core sample assembly 300 may be diverted at a plurality of points using bypass valves 24 and outlet pipe 26 in order to regulate the pore gas pressure (e.g., the establishment of the initial pore pressure) in the sample 30 inside the sample assembly 300 which is placed in the pressure vessel 50; the inlet 40 and outlet 42 on the sample assembly 300 (as shown in FIG. 2) being connected through couplings on the wall or the end caps of the pressure vessel to the pressure lines (such as 28) that are connected the inlet pump 16 and outlet pump 18. The pressure vessel 50 may also be equipped with additional temperature and pressure gauges such as gauge 34, which may be in direct contact with the shale sample 30.

Figure 3:
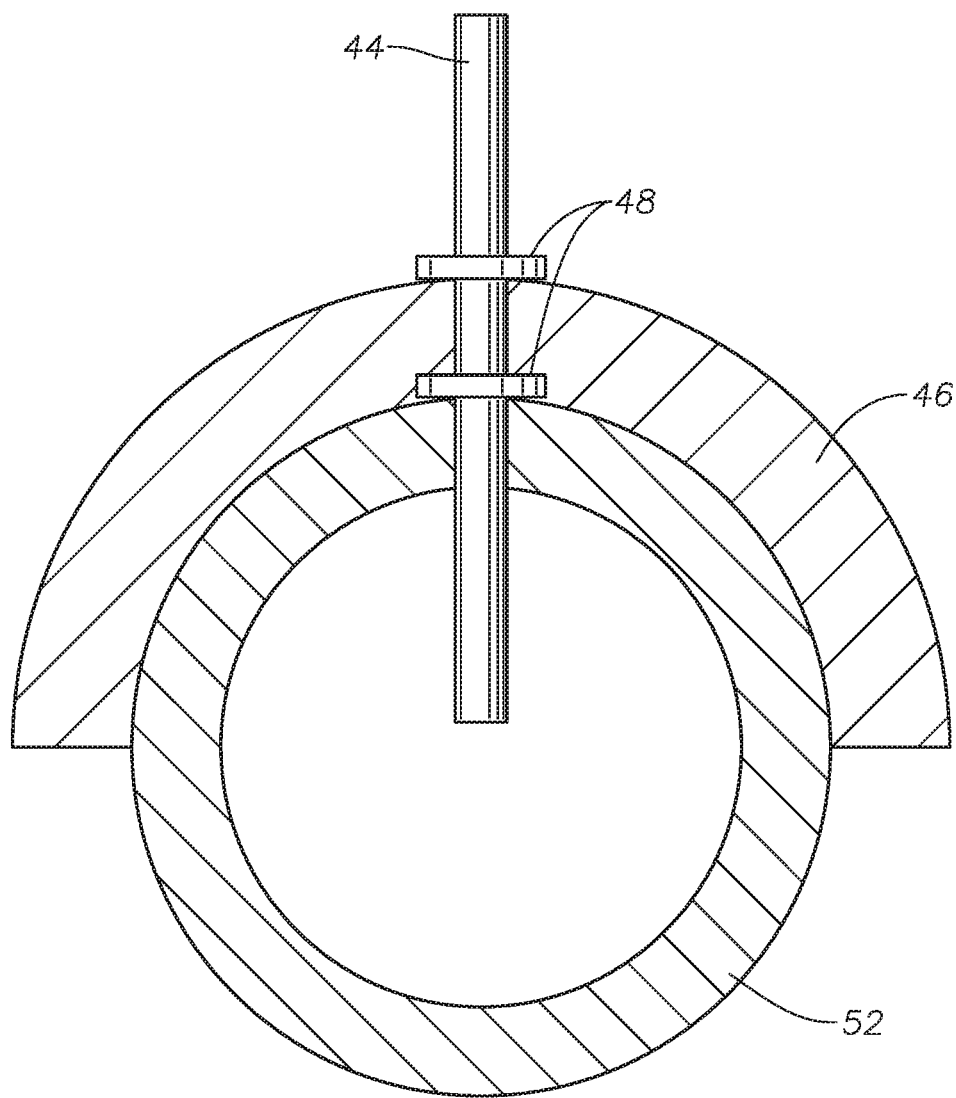
FIG. 3 illustrates an example apparatus for determining permeability and porosity of a subsurface formation, according to one example embodiment of the disclosure.

FIGS. 2A-2D illustrate in further detail an example set up for arranging the shale sample assembly 300 in the pressure vessel 50. As illustrated, the shale sample 30 is first inserted into a sleeve 52 having a length, a diameter, a first open end 60, and a second open end 70. The shale sample may be enclosed in the sleeve 52 using a first end piece 42 adapted to be inserted into the first open end 60 and a second end piece 40 adapted to be inserted into the second open end 70 of the sleeve 52. A through hole or a port for pressure measurement 65 is formed through the body of the sleeve 52 and into the body of the sample 30 so as to insert a tubing, such as a tubing 44. A half sleeve 46 may be disposed on the sleeve 52, and the half sleeve may include a second hole corresponding to the first hole 65 on the first sleeve. The tubing 44 may include a temperature gauge 34 and a pressure gauge 32 as illustrated in FIG. 1, for example. The tubing 44 is inserted through the first hole, the second hole, and into the body of the sample 30. An anchoring device 48, for example, may be used for securing the tubing 44 to the half sleeve 46, thereby forming an assembly. Other fastening devices, such as ring clamps, may be used to secure the half sleeve 46 and the sleeve 52. FIG. 3 illustrates a cross-sectional view of the apparatus in FIG. 2D where steel tubing 44 is inserted through the half sleeve 46, sleeve 52, and secured using anchoring devices 48. According to one example embodiment, sleeve 52 and half sleeve 46 may include at least one of rubber and a polymeric material. According to another example embodiment, an inner diameter of the half sleeve 46 may be smaller than the outer diameter of the sleeve 52. According to another example embodiment, a length of the half sleeve 46 is equal to or less than the length of the sleeve 52.

Figure 4A:
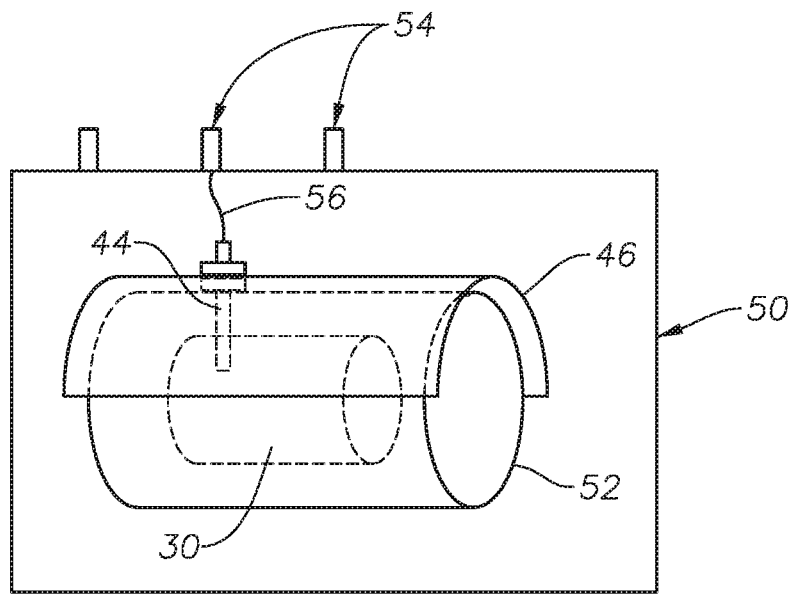
FIGS. 4A and 4B illustrate example apparatuses for determining permeability and porosity of a subsurface formation, according to some example embodiments of the disclosure.
Figure 4B:
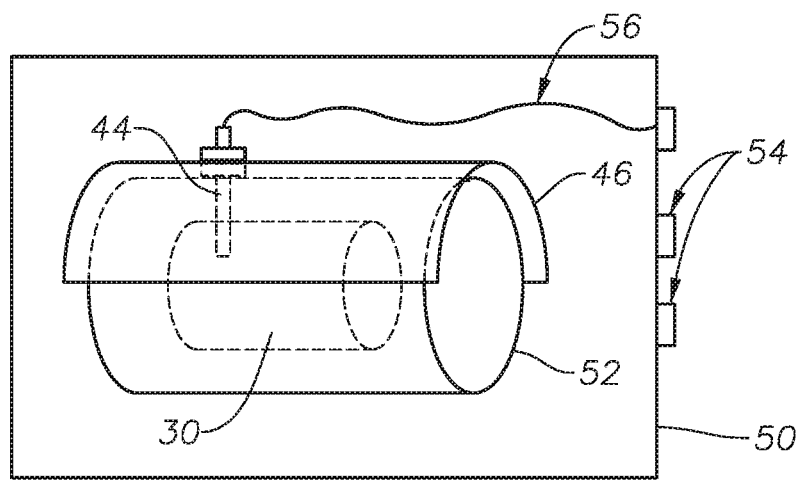

After the sleeve 52 is secured for preventing leakage from the port of pressure measurement 65, the assembly is disposed in the pressure vessel 50, as illustrated in FIG. 4A, for example. The pressure vessel 50 may include a plurality of pressure taps such as 54, each of which to be connected a pressure measurement location along the rock sample. In this case, multiple measurement locations along the rock sample may be instrumented according to the procedure described in FIGS. 2 and 3. The tubing may also include a temperature gauge 34. According to one example embodiment, pressure gauge 32 connected to 44 may be coupled to one of the pressure taps 54 using a flexible line 56.

Analytical Method for Determining Permeability and Porosity of a Subsurface Formation The following sections provide an example method for determining permeability, k, and porosity of a subsurface formation using the system 10 illustrated in FIG. 1. The method is based on a new analytical solution to one-dimensional gas flow under certain boundary and initial conditions, which will be described in further detail below. The governing mass balance equation for gas flow may be given by Equation 1 as follows.

$$\frac{\partial m}{\partial t} = \frac{\partial}{\partial x}\left(\frac{k\rho}{\mu}\frac{\partial p}{\partial x}\right) \qquad (1)$$

where t is time, x is the spatial coordinate (a distance from the inlet of the sample along its axis), k is the permeability, $\mu$, $\rho$, and p are gas viscosity, density and pressure, respectively, (note k, $\mu$, $\rho$, are functions of p) and m is the total gas mass per unit volume of the porous medium or apparent gas density, which may be given by Equation 2 as follows.

$$m = \phi\rho + (1-\phi)\rho_a \qquad (2)$$

where $\phi$ is porosity and $\rho_a$ is adsorbed gas mass per unit volume of solid phase or the subsurface formation. For conservative gases, the second term on the right hand of Equation 2 can be considered to be zero.

In Equation 1, the storage term can be rewritten as $$\frac{\partial m}{\partial t} = \frac{dm}{dp}\frac{\partial p}{\partial t} \quad (3)$$

The present method may relate to isothermal conditions, and therefore m may be considered a function of pressure only. The method may also include relatively high confining stress such that the effect of mechanical deformation due to pore gas pressure change can be ignored. Accordingly, the contributions of gas density change in pressure to storage can be given by Equation 4 as follows.

$$\frac{dm}{dp} = \phi\frac{d\rho}{dp} + (1-\phi)\frac{d\rho_a}{dp} \quad (4)$$

Taking into consideration an infinite long shale sample in the form of a cylinder/column with gas flow from the inlet (x=0) and subject to the following boundary and initial conditions:

$p(x,t)=p_i$ $(x \geq 0, t=0)$ $p(x,t)=p_0$ $(x=0, t>0)$ $p(x,t)=p_i$ $(x \to \infty, t>0)$ (5)

where $p_i$ is the initial pressure inside the measurement system before the elevated upstream pressure, $p_0$, is applied.

Using the transformation $$\lambda = xt^{-\frac{1}{2}} \quad (6)$$

Equations 5 and 1 can be transformed as follows.

$$p(\lambda) = p_i \quad (\lambda \to \infty) \atop p(\lambda) = p_0 \quad (\lambda = 0) \quad \text{and} \quad (7)$$

$$-\frac{\lambda}{2}\frac{dm}{dp}\frac{dp}{d\lambda} = \frac{d}{d\lambda}\left[D(p)\frac{dp}{d\lambda}\right] \text{ where} \quad (8)$$

$$D(p) = \frac{k\rho}{\mu} \quad (9)$$

Equation 8 is an ordinary differential equation with a as the only independent variable.

Directly integrating Equation 8 for the interval ($\lambda$, $\infty$) yields $$D(p) = -\frac{\int_{p_i}^{p}\frac{\lambda}{2}\frac{dm}{dp}dp}{\frac{dp}{d\lambda}} \quad (10)$$

It indicates that $D(p)$ can be fully determined when $p(\lambda)$ is known.

Based on the gas mass balance, the cumulative gas flow into the column (at x=0) can be determined using Equation 11 as follows.

$$M(t) = \quad (11)$$
$$A\int_0^\infty (m-m_i)dx = A(m-m_i)x\Big|_0^\infty - A\int_{p_0}^{p_i}x\frac{dm}{dp}dp = A\int_{p_i}^{p_0}x\frac{dm}{dp}dp$$

where A is the cross-sectional area of the shale column. Combining Equations 11 and 6 gives $$M(t) = \left(A\int_{p_i}^{p_0}\lambda\frac{dm}{dp}dp\right)t^{\frac{1}{2}} = Bt^{\frac{1}{2}} \quad (12)$$

where B is a slope for the curve of M(t) versus $t^{1/2}$. Combining Equations 4 and 12 gives $$\phi = \frac{B - A\int_{p_i}^{p_0}\lambda\frac{d\rho_a}{dp}dp}{A\int_{p_i}^{p_0}\lambda\frac{d(\rho-\rho_a)}{dp}dp} \quad (13)$$

Equations 10 and 13 may be used for estimating gas permeability and porosity, according to one or more example embodiments of the disclosure.

As illustrated above, for an infinite long shale column with a uniform initial pore gas pressure, one can directly estimate the porosity and permeability as a function of pore gas pressure using Equations 10 and 13 from measurement of M(t) and p($\lambda$) obtained under a constant pressure at the column inlet. It should be noted, however, that the gas compressibility and adsorption parameter, which are functions of pore gas pressure, in these equations may be independently determined or estimated from other tests or existing literature. The latter may not be involved if gas used for a test is not reactive.

The test method is consistent with initial and boundary conditions used to obtain Equations 10 and 13 and M(t) and p($\lambda$) can be effectively and reliably measured from a test run. Initially, shale column 30 with a confining stress has a uniform gas pore-pressure $p_i$. The confining stress may be significantly higher than the range of pore gas pressure used in the test such that mechanical deformation due to pore gas pressure variation can be ignored. The column 30 may be about 4" long such that it is long enough to be treated as infinite long for a certain period of test time. The upstream gas reservoir of the shale column 30 may then be connected to pump 16 with precise pressure and/or flowrate control. The upstream pressure of the core column 30 may be maintained as a constant $p_0$ by the pump 16. The pressure range between $p_i$ and $p_0$ covers the range of practical interest or the range in which the pressure dependence is important. Cumulative gas mass flow rate into the column inlet, M(t), may be monitored. The pore gas pressure may be measured as a function of time at a given location of shale column that can be set any location except two ends, preferably about 1" from the column inlet. From the transformation given in Equation 6, p($\lambda$) can be obtained from the pressure measurements. The pressure at outlet of the column 30 is measured to monitor pore gas pressure breakthrough. Pressure breakthrough is considered to occur at the outlet when pressure increases by about 0.1 psi. It should be noted, however, that after pressure breakthrough, the boundary effect from the downstream may be propagated to the measurement point. After that time ($t_c$), the length of column 30 cannot be treated as infinite anymore. Thus only pressure data before that time ($t_c$) can be used to calculate $p(\lambda)$.

The time $t_c$ can be estimated using Equation 14 as follows.

$$t_c = t_b \left[ 1 + \left( \frac{L_b}{L} \right)^2 \right] \quad (14)$$

where $t_b$ is the time of the pressure breakthrough at the outlet of column 30, L is the length of shale column 30, and $L_b$ is the distance between a pressure measurement location and column outlet. The above equation may be obtained by assuming D(p) in Equation 9 to be constant. In this case, the travel distance of diffusion front resulting from outlet disturbance may be proportional to the square root of the time since the pressure breaks through at the outlet.

Figure 5:
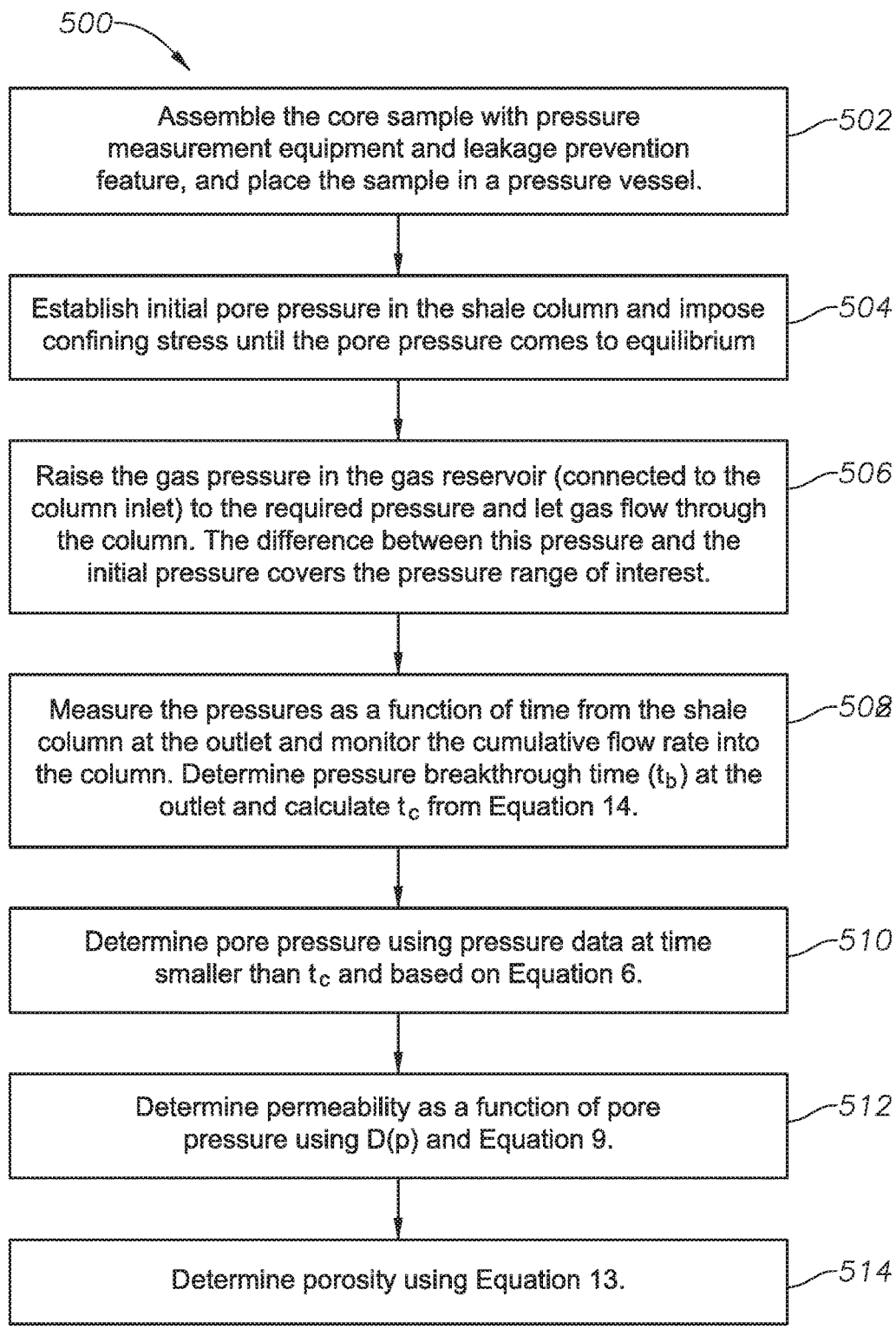
FIG. 5 shows a flow chart illustrating example operations in a method for determining permeability and porosity of a subsurface formation, according to one example embodiment of the disclosure.

Example Method for Determining Permeability and Porosity of a Subsurface Formation Turning now to FIG. 5, illustrated is a flow chart showing example operations in a method 500 for determining permeability and porosity of a subsurface formation, according to one example embodiment of the disclosure. The method uses only one pressure measurement location between the inlet and the outlet of a shale column. However, this is only for illustration purposes, and the method 500 may include pressure measurement at multiple locations along the length of the shale column. While the theory requires only one location to make the pressure measurements as a function of time, pore gas pressures at two or more locations may be measured for reasons like achieving better resolution for $p(\lambda)$. It should be noted, however, that $p(\lambda)$ can be constructed with pressure measurements at different locations. At each measurement location, a small hole with diameter of 1/16" or less and with a depth to about the center of the shale column 30 may be drilled such that shale pore gas pressure can be reliably measured and at the same time, a small hole may not introduce a considerable disturbance to the gas flow along the column.

At operation 502, the core sample may be assembled with pressure measurement equipment and leakage prevention feature, and the sample is placed in a pressure vessel, as illustrated in FIG. 1, for example. At operation 504, an initial pore gas pressure may be established in the shale column and confining stress may be imposed until the pore gas pressure becomes equilibrium. At operation 506, the pore gas pressure in the gas reservoir connected to the column inlet may be raised to the required pressure so that gas may flow through the column. The difference ($p_o - p_i$) between this pressure and the initial pressure covers the pressure range of interest. At operation 508, the pressures may be measured as a function of time from the shale column and at the outlet and monitor the cumulative flow rate into the column. At this point, the pressure breakthrough time ($t_b$) at the outlet may be determined and $t_c$ can be calculated using Equation 14 as follows.

$$t_c = t_b \left[ 1 + \left( \frac{L_b}{L} \right)^2 \right]$$

At operation 510, $p(\lambda)$ may be determined using pressure data at time smaller than $t_c$ and based on Equation 6 as follows.

$$\lambda = xt^{-\frac{1}{2}}$$

At operation 512, D(p) may be determined based on Equation 10 and using $p(\lambda)$ obtained from operation 510 as follows.

$$D(p) = \frac{\int_{p_i}^{p} \frac{\lambda}{2} \frac{dm}{dp} dp}{\frac{dp}{d\lambda}}$$

In Equation 10, the derivative $dp/d\lambda$ can be estimated from $dp/dt$:

$$\frac{dp}{d\lambda} = -\frac{dp}{dt} \frac{2t^{3/2}}{x} \quad (15)$$

It may be more convenient to estimate dp/dt because pressure is directly measured at location x as a function of t. The values of dp/dt can be estimated using the finite difference method with time interval of 1 second or less.

At operation 512, the permeability, k, can be determined as a function of pore gas pressure using D(p) and Equation 9 as follows.

$$D(p) = \frac{k\rho}{\mu}$$

At operation 514, the porosity may be determined with $p(\lambda)$ obtained from operation 508 and Equation 13 as follows.

$$\phi = \frac{B - A \int_{p_i}^{p_0} \lambda \frac{d\rho_a}{dp} dp}{A \int_{p_i}^{p_0} \lambda \frac{d(\rho - \rho_a)}{dp} dp}$$

Figure 6:
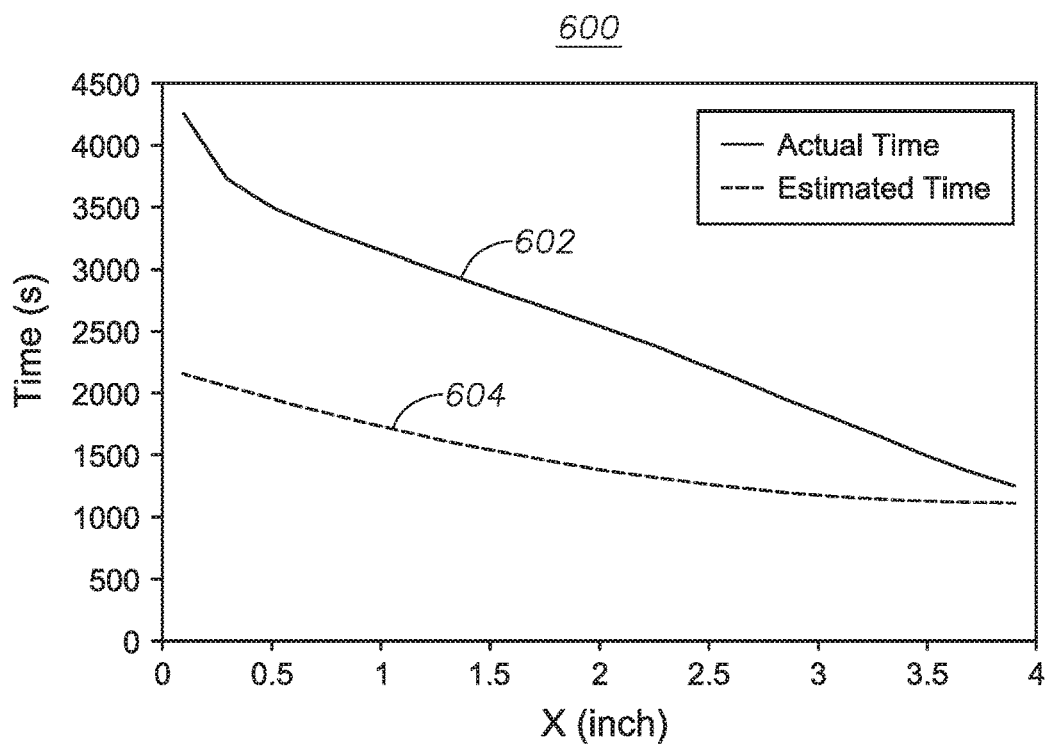
FIG. 6 shows a graphic illustrating simulated time values when the boundary effect occurs (actual time) and estimated time at different locations along a shale formation sample, according to one example embodiment of the disclosure.

The above method is based on an analytical solution for infinitely long column. However, in the experimental data a 4" long shale column, not a finitely long column, is used, and to make sure that the infinitely long column assumption practically holds, pressure data before time $t_c$ given in Equation 14 may be used. FIG. 6 shows a graphic illustrating simulated time values 600 (based on Equation 1 and related boundary and initial conditions) when the boundary effect occurs (actual time from simulation) 602 and estimated time (from Equation 14) 604 at different locations along a shale formation sample, according to one example embodiment of the disclosure. The initial pore gas pressure in a sample may be 100 psi. Pressure at the inlet may be instantaneously raised to 1000 psi at t>0. Gas density and viscosity in Equation 1 may be treated as functions of pore gas pressure. Two columns with lengths of 4" and 12" are used in the simulations. No pore gas pressure breakthrough is observed for the long column during the test time periods; thus it can be treated as an infinitely long column. The simulated pressures at different locations for both columns are compared. The outlet boundary effect is considered to occur at a time when the pressure difference for the two columns at a location is larger than 0.1 psi. FIG. 6 shows simulated time when the boundary effect occurs 602 and the time estimated 604 from Equation 14 at different locations along the column. Clearly, estimates from Equation 14 are smaller than the simulated time values. Thus, Equation 14 can be considered to be on the conservative side. It is reliable to treat pressure data collected for $t<t_c$ as those corresponding to an infinitely long column. As a result, for a 4-inch long shale sample, the no-flow boundary effect can be minimized at X=1 inch. The valid time period for pressure measurement (0-3000 s) can cover a wide pressure range (100-750 psi) for the given example.

Figure 7:
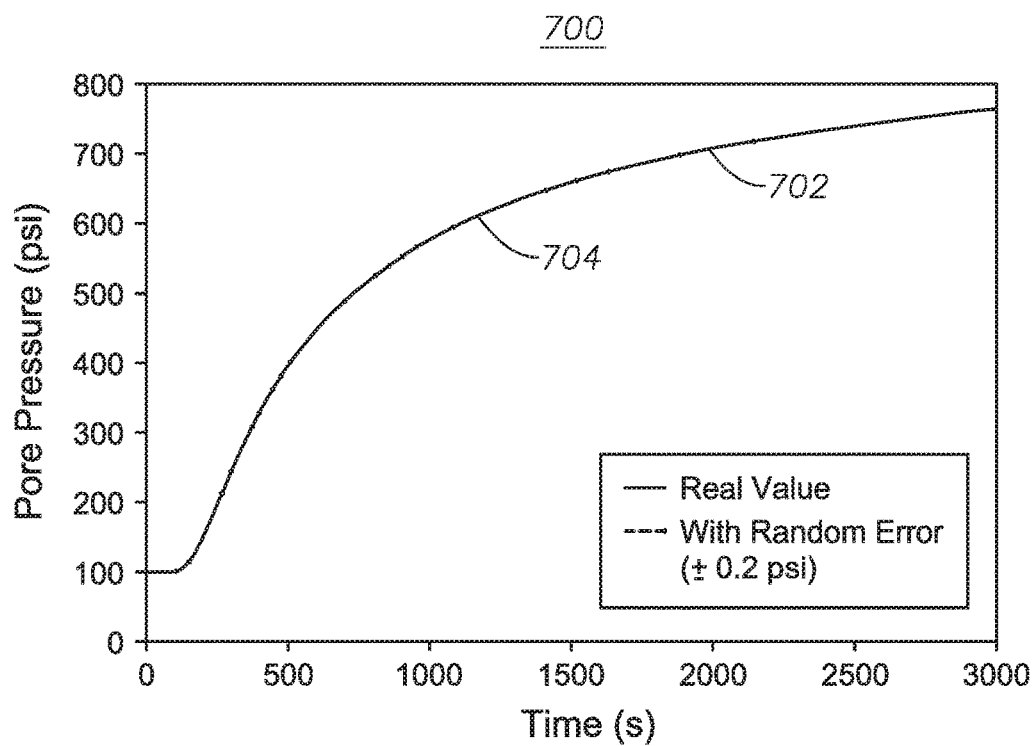
FIG. 7 shows a graphic illustrating simulated gas pore gas pressure, real value and with random error of +/−0.2 psi, as a function of time at the core location about one inch away from the inlet, according to one example embodiment of the disclosure.

Numerical experiments are also conducted to check if the test procedure gives the "true" pressure-dependency of shale gas permeability. In a numerical experiment, the "true" permeability is that used as model input. Observed pressure data from the location about 1" away from the inlet are used and random errors with magnitude of 0.2 psi are added to the simulated pressures to consider the pressure measurement errors. FIG. 7 shows a graphic illustrating simulated gas pore gas pressure 700, real value 702 and with random error of +/−0.2 psi 704, as a function of time at the core location about one inch away from the inlet, according to one example embodiment of the disclosure. The addition of random error does not make considerable difference in the pressure distribution because pressure measurement error is generally small.

As indicated by the line 602 in FIG. 6, the time when the no-flow boundary affects the pressure response in upstream locations increases with the distance to the no-flow boundary. So in order to ensure enough time for valid measurements, the pressure gauge should be put in a reasonable distance away from the boundary. However at the same time, it should not be too close to the inlet because the pressure response there increases from $p_i$ to $p_0$ too fast. In the present method, the measurement location is at X=1 inch.

While doing the actual measurements, an estimated time for valid measurements can be calculated using Equation 14. The blue line 604 (calculated from Equation 14) in FIG. 6 indicates that it is a conservative estimation and thus can be safely used in practice.

Figure 8:
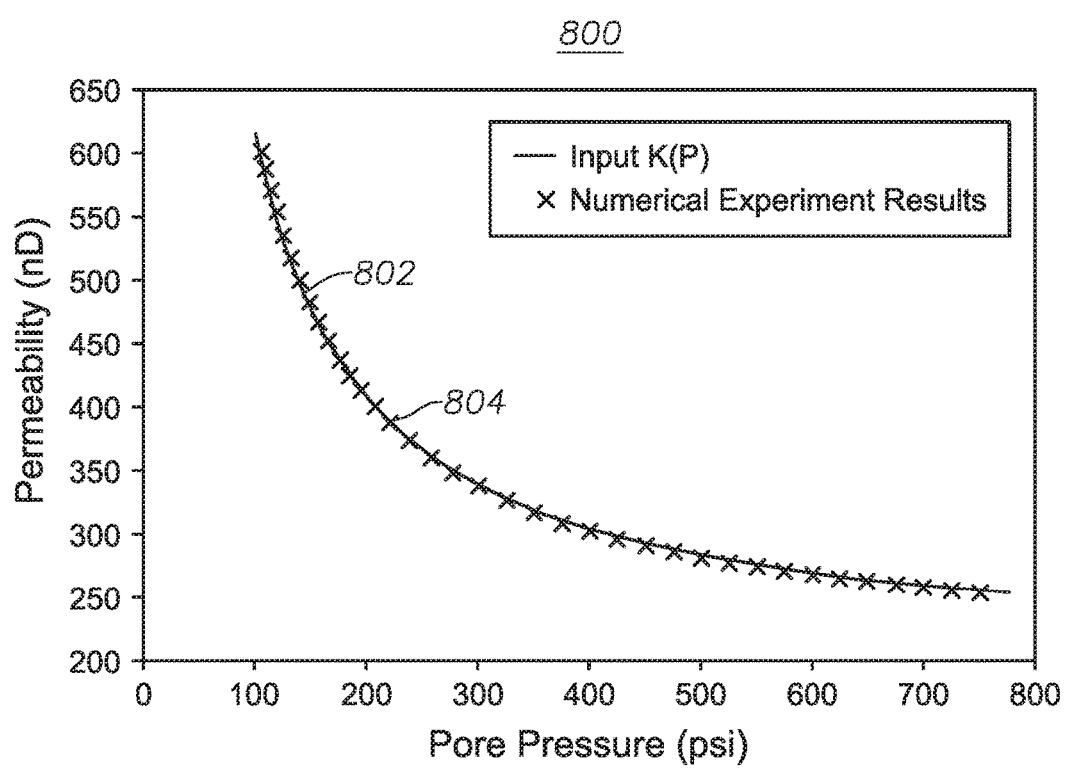
FIG. 8 shows a graphic illustrating comparison between the true permeability as a function of pore gas pressure and the permeability from numerical experiment results, according to one example embodiment of the disclosure.

FIG. 8 shows a graphic illustrating comparison between the true permeability as a function of pore gas pressure and the permeability from numerical experiment results, according to one example embodiment of the disclosure. As shown in the graph 800 in FIG. 8, results 804 based on the laboratory test procedure discussed in the above section with input k(p) and pressure data from numerical experiments are almost identical to the "true" values 802 (or input k(p)), indicating that the proposed procedure is accurate and reliable. It can be observed that they are highly consistent with each other, which also means that the recorded pressure response is very close to that in the theoretical model and the boundary effect is minimized at location X=1 inch.

Computer Readable Medium

Figure 9:
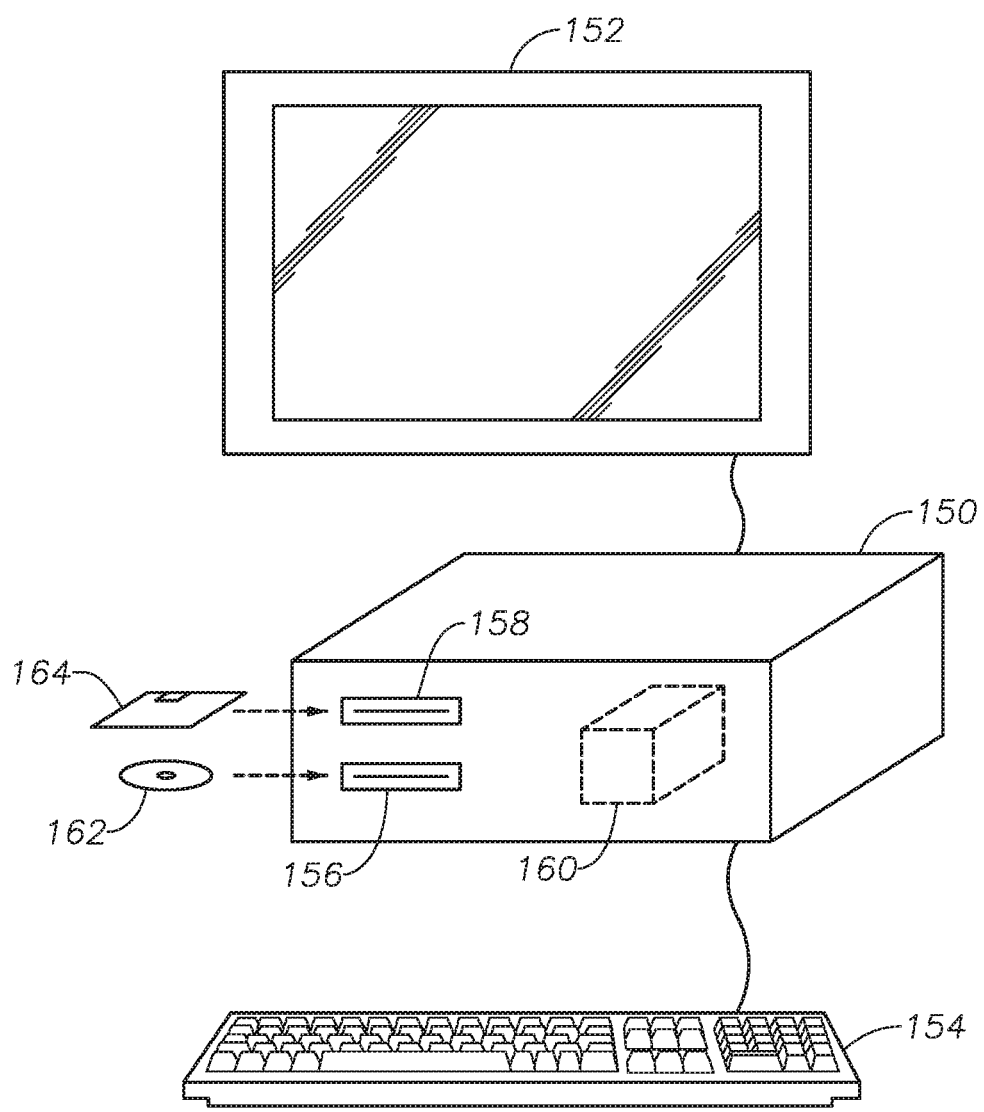
FIG. 9 shows a programmable computer and various forms of computer readable media, according to some example embodiments of the disclosure.

In another example embodiment, the invention relates to computer programs stored in computer readable media. Referring to FIG. 9, the foregoing process as explained with reference to FIGS. 1-8 can be embodied in computer-readable code. The code can be stored on, e.g., a computer readable medium, such as a floppy disk 164, CD-ROM 162 or a magnetic (or other type) hard drive 160 forming part of a general purpose programmable computer. The computer, as known in the art, includes a central processing unit 150, a user input device such as a keyboard 154 and a user display 152 such as a flat panel LCD display or cathode ray tube display. According to this aspect of the invention, the computer readable medium includes logic operable to cause the computer to execute acts as set forth above and explained with respect to the previous figures. The non-transitory computer-readable medium having computer executable instructions cause a computer to perform the operations of reading a measurement of a first pore gas pressure, $p_i$, inside a sample assembly 300 comprising a sample of a subsurface formation, gas, and a pressure gauge. The instructions also include reading a measurement of a second pore gas pressure, $p_o$, applied to the inlet of a sample, where the second pore gas pressure is greater than the first pore gas pressure. The instructions also include reading a measurement of a third pore gas pressure, p, at location x at time t in the sample, and determining a total gas mass per unit volume of the subsurface formation, m. The instructions also include determining a permeability of the subsurface formation, k, based at least in part on the first pore gas pressure, the second pore gas pressure, the third pore gas pressure, and the gas density.

The computer executable instructions further cause the computer to perform the operation of determining the transport parameter of the subsurface formation, D(p), using a first formula:

$$D(p) = \frac{\int_{p_i}^{p} \frac{\lambda}{2} \frac{dm}{dp} dp}{\frac{dp}{d\lambda}}$$

where $p_i$ is the first pore gas pressure inside the sample in assembly 300 before the second pore gas pressure $p_o$ is applied, p is the third pore gas pressure at location x at time t, m is the total gas mass per unit volume of the subsurface formation, and $\lambda$ is an independent variable calculated using the formula $xt^{-1/2}$. Then permeability can be determined from D(p) using Equation 9.

The computer executable instructions further cause the computer to perform the operation of determining the total gas mass per unit volume of the subsurface formation, m, using a second formula:

$$m = \phi \rho + (1-\phi) \rho_a$$

where $\phi$ is porosity of the subsurface formation, $\rho$ is gas density of the natural gas, and $\rho_a$ is adsorbed gas mass per unit volume of the subsurface formation.

The computer executable instructions further cause the computer to perform the operation of determining the porosity $\phi$ of the subsurface formation using a third formula:

$$\phi = \frac{B - A \int_{p_i}^{p_0} \lambda \frac{d\rho_a}{dp} dp}{A \int_{p_i}^{p_0} \lambda \frac{d(\rho - \rho_a)}{dp} dp}$$

where A is a cross-sectional area of the sample, and B is a slope of a curve of the cumulative gas flow into the sample at x=0 versus $t^{1/2}$.

The computer executable instructions further cause the computer to perform the operation of determining the slope of the curve, B, using a fourth formula:

$$B = A \int_{p_i}^{p_0} \lambda \frac{dm}{dp} dp$$

Methods according to the invention may provide improved estimates of permeability as a function of pore gas pressure and porosity of subsurface rock formations. Analytical models used to measure pressure-dependent gas permeability of shale are disclosed. Example methods and systems to measure shale gas permeability as a function of pore gas pressure are disclosed. The advantages of new approach over the currently available ones include that it measures pressure-dependent gas permeability more efficiently using a single test run and without any presumption regarding a parametric relationship between gas permeability and pressure. In addition, the current invention also allows for estimating shale porosity from the related measurements.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

The invention claimed is:

1. An apparatus for determining gas permeability of a subsurface formation, comprising:
   a first sleeve having a length, a diameter, a first open end, and a second open end;
   a first end piece adapted to be inserted into the first open end and a second end piece adapted to be inserted into the second open end of the first sleeve;
   a first hole formed through the first sleeve and into a body of a sample of the subsurface formation housed in the first sleeve;
   a half sleeve disposed on the first sleeve, the half sleeve having a second hole corresponding to the first hole on the first sleeve;
   a tubing comprising a pressure gauge, the tubing inserted through the first hole, the second hole, and into the body of the sample;
   an anchoring device for securing the tubing to the first sleeve and half sleeve, thereby forming a sample assembly; and
   a pressure vessel for receiving the sample assembly, the pressure vessel comprising at least two ports connecting the sample to at least one pump with at least one pressure gauge, at least one port for applying a confining pressure, and at least one port for measuring pressure located at a known location along the sample, wherein determining gas permeability of the subsurface formation comprises:
   positioning the sample in the pressure vessel comprising a fluid and the at least one pressure gauge;
   measuring a first pore gas pressure, $p_1$, of a gas at a location, x, along the sample;
   applying a predetermined second pore gas pressure, $p_0$, to an inlet of the sample, the second pore gas pressure being greater than the first pore gas pressure;
   measuring a third pole gas pressure, p, as a function of time, t, at a location, x, along the sample in the pressure vessel;
   in a computer, determining a gas density or total gas mass per unit volume of the subsurface formation, m; and
   in the computer, determining the gas permeability of the subsurface formation, k(p), based at least in part on the first pore gas pressure, the second pore gas pressure, the third pore gas pressure as a function of time, and the gas density.

2. The apparatus of claim 1, wherein the first sleeve and the half sleeve comprise at least one of rubber and a polymeric material.

3. The apparatus of claim 1, wherein an inner diameter of the half sleeve is smaller than the outer diameter of the first sleeve.

4. The apparatus of claim 1, wherein a length of the half sleeve is equal to or less than the length of the first sleeve.

5. The apparatus of claim 1, wherein the fluid inside the pressure vessel comprises gas, water, or oil.

6. The apparatus of claim 1, wherein the tubing further comprises a temperature gauge.

7. The apparatus of claim 1, wherein the pressure gauge is coupled to the pressure tap using a flexible line.

8. The apparatus of claim 1, further comprising:
   an inlet pump configured to pump gas from a first gas tank into the sample assembly inside the pressure vessel, an outlet pump configured to store gas from the sample assembly inside the pressure vessel into a second gas tank, and gas in the gas tanks, the sample, the pressure lines, and the pumps.

9. The apparatus of claim 1, wherein the step of determining a transport parameter of the subsurface formation further comprises:
   determining a transport parameter of the subsurface formation, D(p), using a first formula:

$$D(p) = \frac{\int_{p_i}^{p} \frac{\lambda}{2} \frac{dm}{dp} dp}{\frac{dp}{d\lambda}}$$

where $\lambda$ is an independent variable calculated using the formula $\lambda = xt^{-1/2}$; and
determining gas permeability k of the subsurface formation from D(p) using $$D(p) = \frac{k\rho}{\mu}$$

where $\mu$ stands for gas viscosity, and $\rho$ for gas density.

10. The apparatus of claim 9, wherein the step of determining gas permeability of the subsurface formation further comprises:
    determining the total gas mass per unit volume of the subsurface formation, m, using a second formula:

$$m = \phi\rho + (1-\phi)\rho_a$$

where $\phi$ is porosity of the subsurface formation, $\rho$ is gas density of the gas, and $\rho_a$ is adsorbed gas mass per unit volume of the subsurface formation.

11. The apparatus of claim 10, wherein the step of determining gas permeability of the subsurface formation further comprises:
    determining the porosity 0 of the subsurface formation using a third formula:

$$\phi = \frac{B - A\int_{p_i}^{p_0} \lambda \frac{d\rho_a}{dp} dp}{A\int_{p_i}^{p_0} \lambda \frac{d(\rho-\rho_a)}{dp} dp}$$

where A is a cross-sectional area of the sample, and B is a slope of a curve of the cumulative gas flow into the sample at x=0 versus $t^{1/2}$.

12. The apparatus of claim 11, wherein the step of determining gas permeability of the subsurface formation further comprises:

determining the slope of the curve, B, using a fourth formula:

$$B = A \int_{P_i}^{P_0} \lambda \frac{dm}{dp} dp.$$

13. The apparatus of claim 1, wherein the subsurface formation comprises at least one of shale, limestone, and sandstone.

* * * * *

UNITED STATES PATENT AND TRADEMARK OFFICE
CERTIFICATE OF CORRECTION

PATENT NO. : 10,436,696 B2
APPLICATION NO. : 16/056596
DATED : October 8, 2019
INVENTOR(S) : Liu et al.

It is certified that error appears in the above-identified patent and that said Letters Patent is hereby corrected as shown below:

In the Claims

In Column 13, Claim 1, Line 55 should read:
-- measuring a third pore gas pressure, p, as a function of --

In Column 14, Claim 9, Lines 19 to 20 should read:
-- The apparatus of claim 1, wherein the step of determining gas permeability of the subsurface formation --

Signed and Sealed this
Twelfth Day of November, 2019

Andrei Iancu
*Director of the United States Patent and Trademark Office*